Aug. 19, 1952 P. SCHNEEBERG Plant Pat. 1,120
ROSE PLANT
Filed June 1, 1951
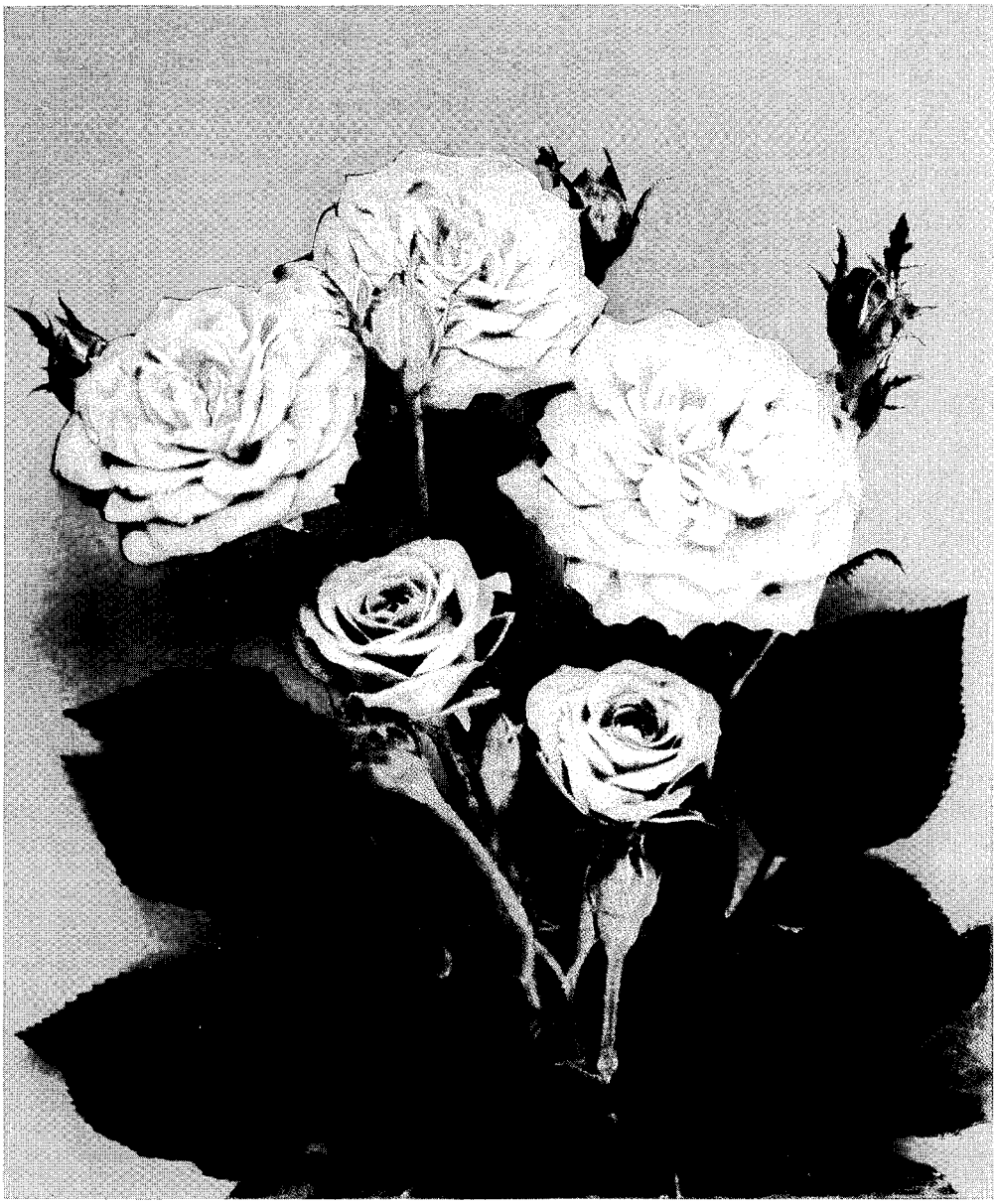
Inventor.
Paul Schneeberg
By: Robb & Robb
Attorneys.

Patented Aug. 19, 1952

Plant Pat. 1,120

UNITED STATES PATENT OFFICE 1,120

ROSE PLANT

Paul Schneeberg, Sayville, N. Y., assignor to Jackson & Perkins Company, Newark, N. Y., a corporation of New York Application June 1, 1951, Serial No. 229,315

1 Claim. (Cl. 47—61)

The present invention relates to a new and distinct variety of rose plant of the large-flowered polyantha class, originating as a sport of the variety known as "Garnette" (unpatented).

In the course of my commercial pursuits as a florist, I discovered the present variety amongst my cultivated plantings of the variety "Garnette" which I was growing in my greenhouse. My attention was drawn to the new variety by reason of the distinctively different color of the blooms on one branch of one of the "Garnette" plants. Thereupon, I promptly removed this branch from the parent plant and budded all of the eyes derived therefrom. From these buddings, I selected the one that was identical to the original sport and preserved the same by further asexual propagation and continued observation.

The parent variety "Garnette" has become an important and commercially successful variety for both indoor and outdoor production of cut flowers, which is largely due to its outstanding characteristic of producing flowers of exceptional long-lasting quality, averaging from ten to fourteen days as cut flowers. This characteristic has been preserved in the present variety and is combined with other important and desirable characteristics which distinguish this new variety from its parent, as well as from all other known roses of its class. The principal dominating distinctions may be listed as follows:

(1) Bushy habit of growth of the plant;

(2) Leathery texture and color of the mature foliage, with young foliage of Victoria Lake color;

(3) Double-serrated foliage, with oval-pointed leaflets;

(4) Freedom of bloom;

(5) Tyrian Rose general tonality of the blooms, giving the blooms a very live appearance, with tints of Tyrian Rose color which are very effective under artificial lights;

(6) Long-lasting quality of the blooms, averaging twelve to fourteen days as cut flowers.

Asexual reproduction of the new variety by budding at Sayville, Long Island, Newark, New York, and Pleasanton, California, shows that the foregoing characteristics come true to form and are established and transmitted through succeeding propagations.

The accompanying drawing shows specimens of the new variety, with the foliage and blooms in different stages of development.

The following is a detailed description of the new variety, with color terminology in accordance with Ridgway's Color Standards and Nomenclature:

Parentage: Sport. Parent—"Garnette" (unpatented).

Classification:

*Botanic.*—Large-flowered polyantha.

*Commercial.*—Floribunda.

*Flower*

(Observations made in the greenhouse at Newark, New York, about mid-morning in the middle of the month of December.)

Blooming habit: Recurrent—continuous.

Bud:

*Size.*—Small.

*Form.*—Ovoid. Is not affected by wet or hot weather.

*Color.*—When sepals first divide—Carmine, Plate 1. When petals begin to unfurl—Tyrian Rose, Plate 12. When half blown—inside of petals: Tyrian Rose, Plate 12; reverse of petals: Tyrian Rose, Plate 12, slightly overcast with Rose Red, Plate 12.

*Sepals.*—Branched. Color—inside: Absinthe Green, Plate 31; outside: Light Cress Green, Plate 31. Curl back when petals begin to unfurl.

*Calyx.* — Shape — pear. Size — small. Aspect—smooth. Odor when rubbed—none. Color—Absinthe Green, Plate 31.

*Peduncle.* — Length — medium. Aspect — prickly. Color—Biscay Green, Plate 17, Strength—erect; slender.

*Opening.*—Opens up well. Is not affected by adverse weather conditions.

Bloom:

*Size.*—Medium. Average size when fully expanded—2½ inches.

*Borne.*—Singly and sometimes in irregular clusters.

*Stems.*—Medium length; strong.

*Form.* — When first open-cupped. Permanence—flattens.

*Petalage.*—Double (full but open center). Number of petals under normal conditions—35 to 40.

(Description made from a freshly opened bloom cut early in the morning and taken indoors or in shade.)

*Color.*—Center of flower—Rose Red, Plate 12. Outer petals—Tyrian Rose, Plate 12, lightly overcast with Rose Color, Plate 12. Base of petals (aiglet)—Light Green Yellow, Plate 5. Inside of petals—Tyrian Rose, Plate 12. Reverse of petals—Tyrian Rose, Plate 12, lightly overcast with Rose Color, Plate 12. General tonality from a distance—Tyrian Rose, Plate 12.

*Discoloration.*—General tonality at end of first day—Tyrian Rose. Plate 12. Second day—Tyrian Rose, Plate 12, lightly overcast with Rose Color, Plate 12. Third day—Tyrian Rose, Plate 12, lightly overcast with Rose Color, Plate 12.

Petals:

*Texture.*—Leathery and crisp. Is not affected by wet or hot weather.

*Appearance.* — Inside — velvety; outside—satiny.

*Form.*—Oval.

*Arrangement.* — Imbricated (regularly arranged shingle-like). Petaloids in center—none.

*Persistence.*—Drop off cleanly.

*Fragrance.*—Moderate. Nature—"Old Rose perfume" (Centifolia).

*Lasting quality.*—On the plant—very long; as cut flower—very long (12 to 14 days).

Genital organs:

*Stamens, anthers.* — Medium size; few. Color—Dresden Brown, Plate 15. Arrangement—regular around styles.

*Stamens, filaments (threads).* — Medium length. Color—Pale Cendre Green, Plate 6.

*Polen.*—Color—Light Buff, Plate 15.

*Styles.*—Bunched; uneven length; medium length; thin.

*Stigmas.*—*Color*—*Light* Chalcedony Yellow, Plate 17.

*Ovaries.*—All enclosed in calyx.

Form: Bush.

Growth: Vigorous; branching.

Foliage: 5 to 7 leaflets.

*Size.*—Medium.

*Quantity.*—Abundant.

*Color.*—New foliage—upper side: Victoria Lake, Plate 1; Under side: Yellowish Oil Green, Plate 5, overcast with Victoria Lake, Plate 1. Old foliage—upper side: Dark Cress Green, Plate 31; under side: Light Cress Green, Plate 31.

*Shape.*—Oval-pointed.

*Texture.* — Upper side — leathery. Under side—velvety. Ribs and veins—ordinary.

*Edge.*—Serrated (saw-toothed).

*Serration.*—Double; sharp.

*Leaf stem.*—Color—Mahogany Red, Plate 2. Under side—smooth.

*Stipules.*—Medium length; bearded.

*Disease resistance.*—Resistant.

Wood:

*New wood.*—*Color*—Yellowish Oil Green, Plate 31. Bark—smooth.

*Old wood.*—Color—Cress Green, Plate 31. Bark—smooth.

Thorns:

*Quantity.*—On main stalks from base and on laterals from stalk—ordinary.

*Form.* — Narrow base; medium length; straight.

*Color when young.*—Rose Doree, Plate 1.

*Position.*—Irregular.

Prickles and short needles: On main stalks and on laterals—none.

I claim:

A new and distinct variety of rose plant of the polyantha class, characterized as to novelty by the bushy habit of growth of the plant, by the leathery texture and color of its mature foliage and the Victoria Lake color of its young foliage, said mature foliage being double-serrated and the leaflets being oval-pointed, by the freedom of bloom, said blooms being Tyrian Rose color in general tonality and tinted with tints of this general color, and by the long-lasting quality of the blooms as cut flowers, substantially as herein shown and described.

PAUL SCHNEEBERG.

No references cited.